(12) United States Patent
Lichtenwalter

(10) Patent No.: US 6,255,053 B1
(45) Date of Patent: *Jul. 3, 2001

(54) DRY BIOCHEMICAL ASSAY PLATE AND METHOD FOR MAKING THE SAME

(75) Inventor: Kay Lichtenwalter, San Jose, CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,710

(22) Filed: Jun. 21, 1999

Related U.S. Application Data

(63) Continuation of application No. 08/412,498, filed on Mar. 28, 1995, now Pat. No. 5,922,534.

(51) Int. Cl.[7] .................................................. G01N 33/543
(52) U.S. Cl. ........................ 435/6; 436/164; 436/518; 436/524; 436/527; 436/531; 436/805; 436/809
(58) Field of Search ............................... 435/6; 436/518, 436/524, 527, 531, 164, 805, 809

(56) References Cited

U.S. PATENT DOCUMENTS

| | | | |
|---|---|---|---|
| 3,642,450 | 2/1972 | Eriksson | 23/253 TP |
| 4,761,378 | 8/1988 | Godsey | 435/293 |
| 4,770,856 | 9/1988 | Uthemann et al. | 422/104 |
| 4,829,010 | 5/1989 | Chang | 422/58 |
| 5,077,210 | 12/1991 | Eigler et al. | 435/176 |
| 5,200,312 | 4/1993 | Oprandy | 435/5 |
| 5,486,452 | 1/1996 | Gordon et al. | 435/5 |
| 5,527,672 | 6/1996 | Mansfield et al. | 435/6 |
| 5,837,832 | 11/1998 | Chee et al. | 536/22.1 |
| 5,922,534 | 7/1999 | Lichtenwalter | 435/6 |

Primary Examiner—Christopher L. Chin
(74) Attorney, Agent, or Firm—Gordon Stewart

(57) ABSTRACT

An assay plate for detecting the presence of a mobile reactant that binds to a immobilized reactant and the methods of making and using the same. An assay plate according to the present invention includes a substrate and at least one dried aliquot of the immobilized reactant, the immobilized reactant being bound to the surface of the substrate. The immobilized reactant binds the mobile reactant when a solution containing the mobile reactant is brought into contact with the immobilized reactant. The mobile and immobilized reactants may be any pair of biological compounds that have a specific affinity for one another For example the reactants may be nucleic acids or antibody-antigen pairs. The preferred embodiment of an assay plate according to the present invention includes a plurality of assay spots, each spot having a different immobilized reactant or concentration thereof The preferred method for fabricating an assay plate according to the present invention includes the is steps of binding the immobilized reactant to the substrate, washing the substrate to remove any immobilized reactant that is not bound to the substrate and then drying the substrate. The dried assay plates are preferably stored in a water-proof container until used. An assay utilizing an assay plate according to the present invention is carried out by bringing a solution containing the mobile reactant into contact with the dried aliquot or aliquots on the assay plate. The assay plate is then washed to removed unbound material and the amount of mobile reactant bound to the washed assay plate determined. In the preferred embodiment of the present invention, the washed assay plate is dried prior to measuring the amount of mobile reactant bound to the washed assay plate.

5 Claims, 1 Drawing Sheet

DRY BIOCHEMICAL ASSAY PLATE AND METHOD FOR MAKING THE SAME

CROSS REFERENCE TO RELATED APPLICATION(S)

This is a continuation of copending application Ser. No. 08/412,498 filed on Mar. 28, 1995, now U.S. Pat. No. 5,922,434.

FIELD OF THE INVENTION

The present invention relates to biochemical assays, and more particularly, to assays in which the presence of a target reactant is determined by measuring the amount of material that is bound to an immobilized reactant.

BACKGROUND OF THE INVENTION

Reactions between biological molecules exhibit an extremely high degree of specificity. It is this specificity that provides a living cell with the ability to carry out thousands of chemical reactions simultaneously in the same "vessel". In general, this specificity arises from the "fit" between two molecules having very complex surface topologies. For example, an antibody binds a molecule displaying an antigen on its surface because the antibody contains a pocket whose shape is the complement of a protruding area on the antigen. This type of specific binding between two molecules forms the basis of numerous biological assays.

For example, nucleic acids are linear polymers in which the linked monomers are chosen from a class of 4 possible sub-units. In addition to being capable of being linked together to form the polymers in question, each unit has a complementary sub-unit to which it can bind electrostatically. In the case of DNA, the polymers are constructed from four bases that are usually denoted by A, T ,G, and C. The bases A and T are complementary to one another, and the bases G and C are complementary to one another. Consider two polymers that are aligned with one another. If the sequences in the polymers are such that an A in one chain is always matched to a T in the other chain and a C in one chain is always matched to a G in the other chain, then the two chains will be bound together by the electrostatic forces. Hence, an immobilized chain can be used to bind the complementary chain. This observation forms the basis of tests that detect the presence of DNA or RNA that is complementary to a known DNA or RNA chain. Such detection forms the basis of a number of medical and/or diagnostic tests.

The methods by which the binding of the mobile reactant to the immobilized component of the system is measured varies with the particular reactants. However, a significant fraction of all of the tests involve the measurement of a fluorescent dye that is associated with either the bound or mobile reactant. The dye may be attached to the reactant from the beginning of the process or it may be added through various chemical steps after the mobile and immobilized reactants have been brought into contact with one another.

Systems for medical diagnosis often involve a bank of tests in which each test involves the measurement of the binding of one mobile component to a corresponding immobilized component. To provide inexpensive test kits, systems involving a matrix of immobilized spots have been suggested. Each spot includes the immobilized component of a two component test such as described above. The fluid to be tested is typically brought into contact with the matrix. After chemical processing, the amount of fluorescence associated with each of the spots in the matrix is measured.

The matrix is typically constructed by dispensing small quantities of the immobilized component onto a substrate such as glass or filter paper. In general, prior art assays utilizing such matrices require that the matrix remain wet from the point in the process at which the components are dispensed through the detection of the fluorescence. This requirement leads to a number of problems when these assay are applied in medical diagnosis. First, the buffer solutions utilized in the processing may contain contaminants that have fluorescent emission bands sufficiently close to those of the fluorescent compound of interest that the stray fluorescence gives rise to errors in the assay. The amount of interference depends on the amount of buffer needed in the particular system. If the ratio of buffer solution to bound fluorescent compound is high, even a small degree of contamination of the buffer solution can generate unacceptable errors.

A second problem with wet assay plates relates to the transportation and storage thereof In medical diagnostic applications, it is anticipated that the assay plates will be prepared by a commercial supplier and shipped to the diagnostic laboratory. The plates would then be stored at the laboratory until needed. The need to provide leak-proof packaging significantly increases the cost of these assay plates.

In addition, the short storage life of wet assay plates at room temperature places additional constraints on the storage and transportation of these assay plates. The biological macromolecules on which these assays are based are easily attacked by various enzymes. These enzymes often appear as contaminants in the various buffer solutions used in preparing and storing the wet assay plates. As a result, the assay plates must be refrigerated to increase their shelf life. The cost of refrigerated storage and transportation significantly increases the cost of assay systems based on wet assay plates. Furthermore, even with refrigerated storage, the useful shelf life of wet assay plates results in significant increases in costs due to the need to discard old assay plates before they are actually used.

A third problem with wet assay plates is the need to read the results of the assay shortly after the chemical processing of the plates. This restricts the reading and interpretation of the results to the laboratory that processed the patient samples with the plates. While this restriction is not very significant in metropolitan settings, it can be a significant problem in rural settings In which the volume of tests is too low to justify the cost of the equipment and personnel needed to read and interpret the assays. As a result, the patient samples are typically sent to a central laboratory for reading and processing. The need for refrigerated transportation of the samples and the inherent time delays in receiving the results of the tests make this solution to the problem less than optimal.

Finally, prior art wet assay plate systems do not provide a means for archiving the assay plates for later examination since the catabolic enzymes described above will destroy the underlying macromolecules even if the assay plates are stored in a refrigerated environment. An assay plate that provided a cost effective archival storage mechanism which would allow the plate to be read again some time after its original processing would be highly desirable both from a research and a legal point of view. Researchers often wish to examine samples from a large population. The samples in question can often be taken from routine assays if archival storage of the routine samples is available. Unfortunately, present archival storage requires storage of the original samples at liquid nitrogen temperatures. The costs inherent in this approach limit the archiving of samples to special studies.

In legal settings, the ability to re-examine tests performed months or years earlier would be of significant benefit in determining the validity of the earlier performed tests. There are many situations in which the validity of such tests determines the outcome in a legal proceeding.

Broadly, it is the object of the present invention to provide an improved assay plate system for performing assays based on the binding of biological macromolecules.

It is a further object of the present invention to provide an assay plate system in which the assay plates do not need to be shipped or stored in a wet state.

It is a still further object of the present invention to provide an assay plate system in which the assay plates may be read and archived in a dry state.

These and other objects of the present invention will become apparent to those skilled in the art from the following detailed description of the invention and the accompanying drawings.

SUMMARY OF THE INVENTION

The present invention comprises an assay plate for detecting the presence of a mobile reactant that binds to a immobilized reactant and the methods of making and using the same. An assay plate according to the present invention includes a substrate and at least one dried aliquot of the immobilized reactant, the immobilized reactant being bound to the surface of the substrate. The immobilized reactant binds the mobile reactant when a solution containing the mobile reactant is brought into contact with the immobilized reactant. The mobile and immobilized reactants may be any pair of biological compounds that have a specific affinity for one another. For example the reactants may be nucleic acids or antibody-antigen pairs. The preferred embodiment of an assay plate according to the present invention includes a plurality of assay spots, each spot having a different immobilized reactant or concentration thereof The preferred method for fabricating an assay plate according to the present invention includes the steps of binding the immobilized reactant to the substrate, washing the substrate to remove any immobilized reactant that is not bound to the substrate and then drying the substrate. The dried assay plates are preferably stored in a water-proof container until used. An assay utilizing an assay plate according to the present invention is carried out by bringing a solution containing the mobile reactant into contact with the dried aliquot or aliquots on the assay plate. The assay plate is then washed to removed unbound material and the amount of mobile reactant bound to the washed assay plate determined. In the preferred embodiment of the present invention, the washed assay plate is dried prior to measuring the amount of mobile reactant bound to the washed assay plate.

DETAILED DESCRIPTION OF THE INVENTION

Figure 1:
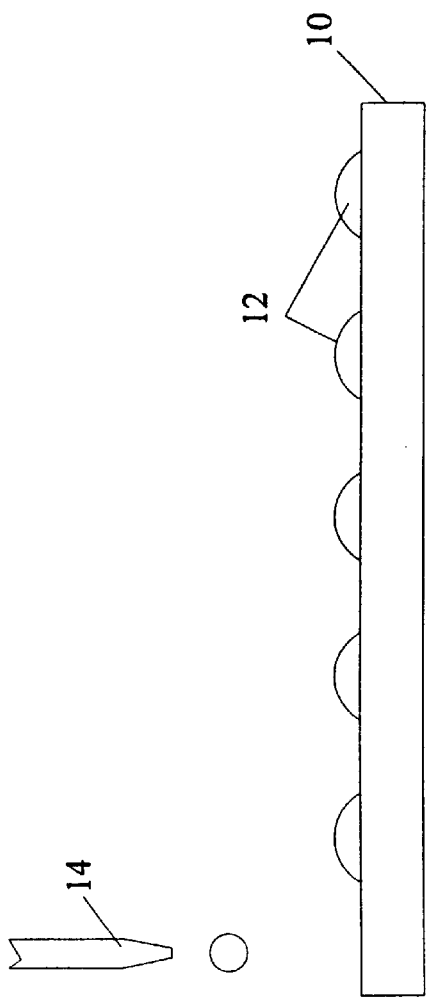
FIG. 1 is a side view of an assay plate according to the present invention.
Figure 2:
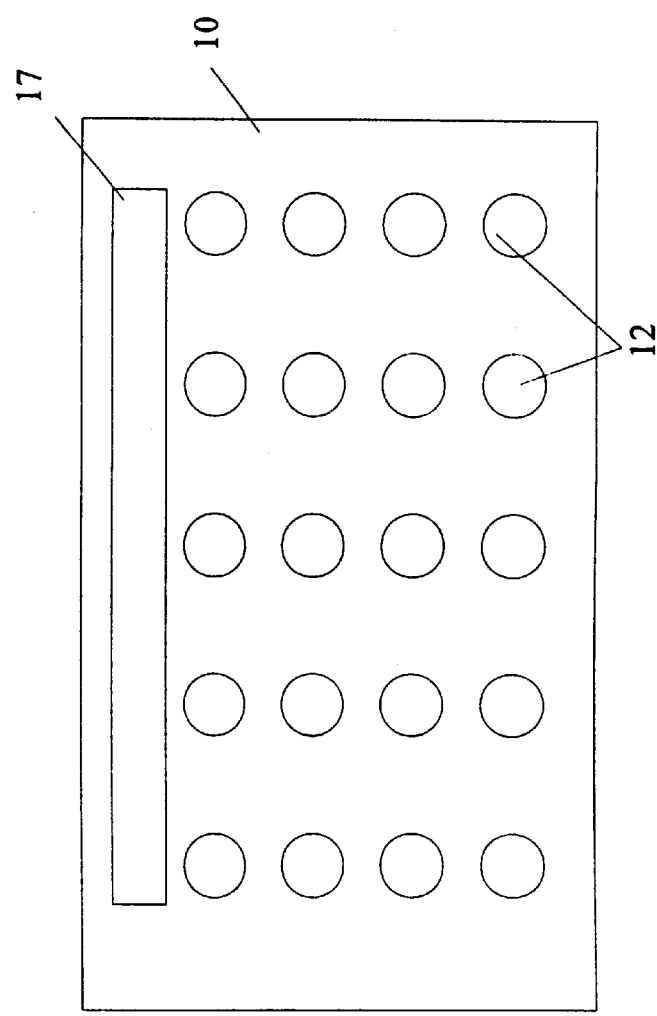
FIG. 2 is a top view of the assay plate shown in FIG. 1.

The present invention may be more easily understood with reference to FIGS. 1 and 2 which are side and top views of a matrix of test spots 12 deposited on a substrate 10. The individual spots are typically dispensed by a dispensing apparatus 14. Each test spot includes one member of a pair of chemical structures that will bind to one another if brought into contact with one another. The chemical species included in the test spot will be referred to as the immobilized species. The other member of the pair will be referred to as the mobile species.

The immobilized species is typically deposited on substrate 10 in a carrier liquid. In principle, each spot includes a different immobilized species or concentration thereof that will become attached to substrate 10. The preferred method for providing the attachment will be discussed in more detail below. The presence of a mobile species is determined by measuring the amount of material bound to the corresponding test spot when a solution to be tested is brought into contact with the test spot. Test plates such as that shown in FIGS. 1 and 2 are designed to test for a plurality of mobile species simultaneously.

The manner in which the test spots are generated may be more easily understood with reference to a test spot for detecting a DNA molecule having a specific nucleotide sequence. As noted above, a single stranded DNA molecule will bind to a second single stranded DNA molecule if the second DNA molecule has a sequence that is complementary to the first DNA molecule. The amount of bound DNA may be measured photometrically by measuring the amount of dye present when the bound test spot is treated with a dye that binds to double stranded DNA molecules. Alternatively, the second DNA molecules can be labeled with a dye that can be measured photometrically.

The present invention is based on the experimental observations that the assay plates may be dried at two key points in the assay process. First, the assay plates may be dried after the immobilized species have been bound to the assay plate. This allows the assay plates to be stored as dry plates. The dry plates may then be used in assays to detect the mobile species by re-hydrating the plates and exposing the plates to the mobile species utilizing the same conventional wet chemistry that is used in the analogous assay system utilizing conventional wet assay plates. After the reactants have bound to the immobilized species and the reaction is complete, the assays may be read by conventional means or as described below. The dried assay plates are found experimentally to have significantly longer shelf-lives than the conventional wet plates, since the degradative process that normally limit the life time of wet plates proceed much slower in the absence of water.

While the assay plates may be read in their final wet state, in the preferred embodiment of the present invention several wash steps are performed with the appropriate buffers to remove any non-specific binding component and the assay plates are once again dried. The dried plates may then be read in a fluorescent detection system without interference from contaminants in the buffers. Alternatively, the dried assay plates may be stored for later reading. This alternative allows the plates to be read at a remote location and/or archivally stored.

Having provided the above overview of the present invention, the manner in which the assay plates are prepared will now be described in more detail. For the purposes of this discussion, it will be assumed that the assay plates are constructed on glass substrates, specifically, fused silica slides and that the immobilized species is a oligonucleotide, either is DNA or RNA. However, procedures for binding other immobilized species will be apparent to those skilled in the art from the following discussion. It should also be noted that the basic chemistry for binding the immobilized species to a glass surface is well known to the art. The following discussion is provided to provide the reader with an appreciation of the procedure.

The process starts with the cleaning of the slides. In the preferred embodiment of the present invention, the slides are sonicated in detergent for 15 minutes. The preferred detergent solution is 5% RBS-35 (Pierce Chemicals)/95% ethanol. The slides are then rinsed for 10 minutes in double distilled water. The slides are then subjected to a concentrated nitric acid wash for 15 minutes followed by a second distilled water rinse. The cleaned slides are dried in two steps. First, the slides are dried with $N_2$. The slides are then placed in an oven at 100° C. for 15 minutes and dried under vacuum.

The cleaned slides are then reacted with amino propyl triethoxy silane (APTES) to provide binding sites for attaching the immobilized species. The surface of the slide is coated with a 1% APTES solution in 95% ethanol. The slides are incubated at room temperature for 45 minutes in a covered petri dish. The slides are then washed in 95% ethanol and dried in $N_2$ at 110° C. for 15 minutes. The drying is preferably carried out by the two step procedure discussed above. The coated slides may be stored in aluminum foil or in a $N_2$ filled chamber.

The immobilized species is then linked to the coated surface via Bis succinimydl suberate-homobifunctional NHS-ester ($BS^3$). This procedure is performed in two steps. First, the immobilized species is linked to the $BS^3$ linker. The linked immobilized species is then attached to the APTES coated surface. The linkage reaction is carried out by mixing 20 $\mu$l of $BS^3$ to 55 nmoles of the immobilized species in a TES buffer and incubating the mniture for 15 minutes at room temperature. The linked immobilized species are then purified on a Nap 25 column (available from Pharmacia).

The linked immobilized species dissolved in a TES buffer at pH 8.0 are then placed on the APTES coated surface as a plurality of "spots" on the surface, each spot containing a different immobilized species or concentration thereof The slides are incubated for 1 hour at room temperature in a moist chamber. Any excess fluid is removed by aspiration. The slides are then washed in TES buffer at pH 8.0. The slides are then dried in $N_2$. In the preferred embodiment of the present invention, the slides are packaged in moisture proof packaging for storage.

The above described attachment scheme utilizes the amino group of the immobilized species as the "hook" for attaching the immobilized species to the slide. Hence, it will be apparent to those skilled in the art that proteins may also be attached via this mechanism. In particular, it will be apparent from the above discussion that assay plates based on immobilized antibodies or antigens may also be prepared utilizing this procedure.

As noted above, the dried slides may be used in place of conventional wet slides at the time the assay for the mobile species is to be performed. A solution containing the mobile species is brought into contact with the surface of dried slide under conditions that permit the binding of the mobile species to the immobilized species. After an appropriate incubation period, the slides are washed to remove any unbound immobilized species. The amount of material bound to the washed slides is then determined by applying a dye that binds to either the bound immobilized-mobile species complex or to the mobile species. For example, in applications in which the mobile and immobile species are both nucleic acids, acridine dyes that insert themselves between the two bound strands of nucleic acid may be used. In the case of antibody-antigen assays, the dye system detects bound antibodies by attaching to the general class of antibodies. This later case involves a number of steps that are conventional in the art, and hence, will not be discussed in more detail here.

It has also been observed experimentally that the slides with the bound dyes may be washed and dried without substantially interfering with the measurement of the bound dye. In fact, dry slides often have lower background readings than slides read in the conventional manner, since any contamination from fluorescent compounds in the buffer solutions normally used in the wet process are substantially reduced. In the preferred embodiment of the present invention, the slides are washed as described above and dried in $N_2$.

The dried slides may be stored for months or even years and read a plurality of times if necessary. This ability to store the final slides allows slides prepared at a remote location to be sent to a central reading location. In addition, the accuracy of tests may be verified at a later time, thus reducing false positives resulting from errors in reading the original reading of the slides. The ability to verify a test result is particularly useful in legal settings in which the validity of test results is often questioned month or even years after the tests were performed.

Various modifications to the present invention will become apparent to those skilled in the art from the foregoing description and accompanying drawings. Accordingly, the present invention is to be limited solely by the scope of the following claims.

What is claimed is:

1. A method for detecting a mobile nucleic acid comprising the steps of:
    providing an assay plate having a dried aliquot of an immobilized nucleic acid bound thereon, said immobilized nucleic acid binding said mobile nucleic acid when both said immobilized nucleic acid and said mobile nucleic acid are in a wet state;
    bringing a solution containing said mobile nucleic acid into contact with said dried aliquot;
    washing said assay plate;
    drying said washed assay plate;
    determining, while the washed assay plate is dry, the amount of mobile nucleic acid bound to said washed assay plate.

2. A method according to claim 1 additionally comprising treating with a dye that binds to one of said immobilized nucleic acid or said mobile nucleic acid.

3. The method of claim 2 wherein the step of treating with dye comprises binding the dye to the mobile nucleic acid prior to bringing the solution into contact with the dried aliquot.

4. The method of claim 2 wherein the step of treating with dye comprises depositing the dye on the dried aliquot after bringing the solution into contact with the dried aliquot.

5. The method of claim 1 wherein the assay plate has multiple dried aliquots thereon of different species or concentration.

* * * * *